United States Patent [19]

Vidal

[11] 4,320,064

[45] Mar. 16, 1982

[54] POLYNUCLEAR RHODIUM CARBONYL COMPLEXES

[75] Inventor: Jose' L. Vidal, Charleston, W. Va.

[73] Assignee: Union Carbide Corporation, New York, N.Y.

[21] Appl. No.: 135,403

[22] Filed: Mar. 31, 1980

[51] Int. Cl.³ ............................................. C07F 15/00
[52] U.S. Cl. ................................ 260/429 R; 423/417; 568/853; 518/701
[58] Field of Search ..................... 260/429 R; 423/417

[56] References Cited

U.S. PATENT DOCUMENTS 4,115,433  9/1978  Cosby et al. .................... 260/429 R
4,199,520  4/1980  Cosby et al. .................... 260/429 R

*Primary Examiner*—Helen M. S. Sneed
*Attorney, Agent, or Firm*—Gary L. Wamer

[57] ABSTRACT

Particular polynuclear rhodium carbonyl complexes are provided which are useful in the production of polyhydric alcohols such as ethylene glycol by the reaction of carbon monoxide and hydrogen. These complexes are rhodium carbonyl cluster compounds comprising twenty-two rhodium atoms in the cluster cage.

8 Claims, 6 Drawing Figures

╫ Edge Bridge Carbonyl

◯ Terminal Carbonyl

• Face Bridge Carbonyl

INFRARED SPECTRA OF RHODIUM COMPOSITION

Example 1

INFRARED SPECTRA OF RHODIUM COMPOSITION
Example 2

INFRARED SPECTRA OF RHODIUM COMPOSITION

Example 16

INFRARED SPECTRA OF RHODIUM COMPOSITION

Example 17

4,320,064

POLYNUCLEAR RHODIUM CARBONYL COMPLEXES

FIELD OF THE INVENTION

This invention is concerned with rhodium carbonyl complexes, their structural characteristics, preparation and use as catalysts. More particularly, this invention provides new rhodium carbonyl cluster compounds of unusally high rhodium nuclearity. The cluster compounds of the invention are useful as catalysts for the conversion of hydrogen and carbon monoxide to alcohols including monohydric alcohols (e.g., methanol) and polyhydric alcohols (e.g., ethylene glycol).

DISCUSSION OF PRIOR ART

In a review article entitled "Transition-Metal Compounds Containing Cluster of Metal Atoms", published in *Quarterly Reviews*, 20, 389–401 (1966), the author, Professor F. A. Cotton, defines metal cluster compounds as follows (at page 389):

"Metal atom cluster compounds can be formally defined as 'those containing a finite group of metal atoms which are held together entirely, mainly, or at least to a significant extent, by bonds directly between the metal atoms even though some nonmetal atoms may be associated intimately with the cluster.'"

Metal cluster compounds comprising carbon monoxide in complex combination with metal atoms are more specifically referred to as metal carbonyl cluster compounds. In accordance with nomenclature adopted by P. Chini in a review article entitled "The Closed Metal Carbonyl Clusters," published in *Reviews* 1968, *Inorganica Chimica Acta*, pages 31-51, the carbonyl groups may be "terminal" (i.e., carbon monoxide is bonded to one metal atom), "edge bridging" (i.e., carbon monoxide bridges two metal atoms), or "face bridging" (i.e., carbon monoxide bridges three metal atoms). In this 1968 review article, P. Chini further states that the only structurally characterized metal carbonyl cluster compound having more than six metal atoms is $[N(CH_3)_4[Rh_{12}(CO)_{30}]]$, and depicts the molecular structure of the cluster dianion, $[Rh_{12}(CO)_{30}]^{2-}$, in FIG. 25 of said article. As far as is known, of the metal carbonyl cluster compounds reported since 1968, the clusters containing the largest number of metal atoms are those in which the metal atoms of the cluster are rhodium or platinum. To date, fully characterized species of such more highly nuclear clusters are the following:

(1) $[Rh_{13}(CO)_{24}H_{5-n}]^{n-}(n=2,3)$ reported by V. G. Albano, A Ceriotti, P. Chini, C. Ciani, S. Martinengo and W. M. Anker, *J. Chem. Soc. Chem. Commun.*, 859 (1975);

(2,3) $[Rh_{14}(CO)_{25}]^{4-}$ and $[Rh_{15}(CO)_{27}]^{3-}$ reported by S. Martinengo, G. Ciani, A. Sironi and P. Chini, *J. Am. Chem. Soc.*, 100, 7096-7098 (1978).

(4) $[Rh_{17}(CO)_{32}(S)_2]^{3-}$, described in U.S. Pat. No. 4,115,433 to J. L. Vidal et al., patented Sept. 19, 1978, and also reported in an article by J. L. Vidal, R. A. Fiato, L. A. Cosby and R. L. Pruett, entitled "$[Rh_{17}(S)_2(CO)_{32}]^{3-}$. 1. An Example of Encapsulation of Chalcogen Atoms by Transition-Metal-Carbonyl Clusters" published in *Inorganic Chemistry*, 17, 2574-2582 (1978); and (5) $[Pt_{19}(CO)_{22}]^{4-}$ reported by P. Chini et al. at the 175th American Chemical Society National Meeting at Anaheim, Calif. (March 1978).

The preparation and structure of this tetraanion is further reported by D. M. Washecheck et al. and A. Ceriotti et al., in *J. Am. Chem. Soc.*, 101, pages 6110–6112 (Sept. 26, 1979). Apparently, a dimer of this cluster has also been prepared; see, *Chemical and Engineering News*, cover and page 30 (Nov. 12, 1979).

Rhodium carbonyl complexes have been reported as useful catalytic materials for the conversion of carbon monoxide and hydrogen to polyfunctional oxygen-containing compounds such as polyhydric alcohols and their ester derivatives. Illustrative of such processes and catalysts are those described in U.S. Pat. No. 3,883,634, to R. L. Pruett et al, patented Sept. 3, 1974 and U.S. Pat. No. 4,133,776 to R. L. Pruett et al, patented Jan. 9, 1979. These patents describe the reaction of hydrogen and carbon monoxide in the presence of rhodium carbonyl complex catalysts at a temperature of between about 100° C. and about 375° C. and at a pressure of between about 500 and 50,000 pounds per square inch absolute (p.s.i.a.) sufficient to produce the aforementioned polyfunctional oxygen-containing compounds. Key products are ethylene glycol and ethylene diacetate. Other products are monohydric alcohols such as methanol and ethanol, and their ester and ether derivatives.

Further, U.S. Pat. No. 3,957,857 to R. L. Pruett et al, prepared May 18, 1976 describes effecting the conversion of carbon monoxide and hydrogen in the presence of a rhodium carbonyl cluster having a particular infrared spectral pattern exhibiting three intense wavelength bands between about plus and minus 10 $cm^{-1}$ of about 1868 $cm^{-1}$, of about 1838 $cm^{-1}$, and of about 1785 $cm^{-1}$. Disclosed as illustrative of two rhodium carbonyl clusters suitable for use in the process of U.S. Pat. No. 3,957,857 are clusters having the empirical formulas, $Rh_6(CO)_{16}$ and $[Rh_{12}(CO)_{30}]^{2-}$, the molecular structure of which are shown at column 2, beginning with line 54 through column 3, line 17 of said patent. An especially useful infrared cell for detecting the existence of rhodium carbonyl clusters having defined infrared spectral characteristics during the course of the manufacture of polyhydric alcohols from carbon monoxide and hydrogen is the cell described in U.S. Pat. No. 3,886,364 to W. E. Walker et al, issued May 27, 1975.

Particular salts of the aforementioned dodecatriacontacarbonyl anion, $[Rh_{12}(CO)_{30}]^{2-}$, wherein the counterions are mono-, di- or tri-valent, and their use in the aforementioned processes are those described in U.S. Pat. Nos. 3,878,214, 3,878,290 and 3,878,292 to W. E. Walker et al. Further, plural metal triacontacarbonyl cluster salts wherein the total number of metal atoms in the cluster portion is no more than twelve, and their use in the aforementioned processes, are described in U.S. Pat. Nos. 3,929,969, 3,974,259 and 3,989,799 to E. S. Brown.

For other developments relating to the formation of ethylene glycol from carbon monoxide and hydrogen in the presence of rhodium carbonyl complexes including rhodium carbonyl clusters, and concerning the utilization of certain solvents, promoters, catalysts, amounts of ingredients, separation of products, catalyst regeneration, recovery methods, and other process improvements, see the list of additional patents and copending applications set-forth in footnoted Table A, below*

TABLE A

| | | |
|---|---|---|
| U.S. Pat. No. | 3,940,432 | Patented February 24, 1976 |
| U.S. Pat. No. | 3,944,588 | Patented March 16, 1976 |
| U.S. Pat. No. | 3,948,965 | Patented April 6, 1976 |
| U.S. Pat. No. | 3,952,039 | Patented April 20, 1976 |
| U.S. Pat. No. | 3,968,136 | Patented July 6, 1976 |
| U.S. Pat. No. | 4,001,289 | Patented January 4, 1977 |
| U.S. Pat. No. | 4,013,700 | Patented March 22, 1977 |
| U.S. Pat. No. | 4,111,975 | Patented September 5, 1978 |
| U.S. Pat. No. | 4,115,428 | Patented September 19, 1978 |
| U.S. Pat. No. | 4,115,433 | Patented September 19, 1978 |
| U.S. Pat. No. | 4,151,192 | Patented April 24, 1979 |
| U.S. Pat. No. | 4,153,623 | Patented May 8, 1979 |
| U.S. Pat. No. | 4,162,261 | Patented July 24, 1979 |
| U.S. Pat. No. | 4,180,517 | Patented December 25, 1979 |
| U.S. Ser. No. | 618,021 | Filed September 30, 1975 |
| U.S. Ser. No. | 715,853 | Filed August 19, 1976 |
| U.S. Ser. No. | 786,584 | Filed April 11, 1977 |
| U.S. Ser. No | 862,554 | Filed December 20, 1977 |
| U.S. Ser. No. | 882,395 | Filed March 1, 1978 |
| U.S. Ser. No. | 882,396 | Filed March 1, 1978 |
| U.S. Ser. No. | 890,969 | Filed March 28, 1978 |
| U.S. Ser. No. | 919,419 | Filed June 27, 1978 |
| U.S. Ser. No. | 919,857 | Filed June 28, 1978 |
| U.S. Ser. No. | 920,828 | Filed June 30, 1978 |
| U.S. Ser. No. | 946,313 | Filed September 27, 1978 |
| U.S. Ser. No. | 946,314 | Filed September 27, 1978 |
| U.S. Ser. No. | 968,371 | Filed December 11, 1978 |
| U.S. Ser. No. | 968,400 | Filed December 11, 1978 |
| U.S. Ser. No. | 9,352 | Filed February 5, 1979 |
| U.S. Ser. No. | 25,093 | Filed March 29, 1979 |
| U.S. Ser. No. | 25,094 | Filed March 29, 1979 |
| U.S. Ser. No. | 56,967 | Filed July 12, 1979 |
| U.S. Ser. No. | 61,465 | Filed July 31, 1979 |
| U.S. Ser. No. | 62,357 | Filed July 31, 1979 |
| U.S. Ser. No. | 71,576 | Filed August 31, 1979 |
| U.S. Ser. No. | 70,003 | Filed August 27, 1979 |
| U.S. Ser. No. | 81,919 | Filed October 4, 1979 |
| U.S. Ser. No. | 85,208 | Filed October 16, 1979 |

None of the aforementioned articles, patents, or applications, however, describe rhodium carbonyl cluster compounds having the high rhodium nuclearity of the particular clusters of this invention.

SUMMARY OF THE INVENTION

The rhodium carbonyl clusters of the present invention are the first characterized examples of rhodium carbonyl complexes having more than twenty rhodium atoms in the molecule. More specifically, the rhodium carbonyl cluster compounds of this invention comprise a cluster cage containing twenty-two rhodium atoms ("Rh-22"). In addition to carbonyl ligands, the compounds may also comprise hydrogen present as hydrido ligands, hydrogen cations (H+), hydronium cations (H$_3$O+), or any combination thereof. In one embodiment, the compounds of the invention are neutral clusters. In another embodiment, the compounds are salts wherein the cluster bears a negative charge and is in association with a cation.

The present invention also provides methods for preparing rhodium carbonyl cluster compounds of high nuclearity such as the Rh-22 carbonyl complexes. In general, such methods comprise reacting a solubilized rhodium source in a solvent-containing liquid phase with carbon monoxide, or a carbon monoxide containing gas (e.g., synthesis gas) at a carbon monoxide pressure from about 1 to about 3 atmospheres and a temperature from about 130° to about 170° C., but these conditions can be more broadly varied as indicated below.

The rhodium carbonyl cluster compounds of this invention are useful as catalytic materials in a variety of processes such as, for example, the hydroformylation of olefins. They are especially effective catalysts in processes directed to the conversion of carbon monoxide and hydrogen to alkane polyols such as ethylene glycol.

BRIEF DESCRIPTION OF THE DRAWINGS

FIG. 1 is a computer ORTEP diagram of the docosarhodium pentatriacontacarbonyl cluster compound, [Rh$_{22}$(CO)$_{35}$H$_x$]$^{n-}$ (n=4, 5), produced in accordance with Example 1, except that the carbonyl ligands have been omitted for the sake of clarity in showing the Rh-22 skeleton of the compound.

FIG. 2 is a schematic representation of the complete structure of the [Rh$_{22}$(CO)$_{35}$H$_x$]$^{n-}$ anionic cluster based on the ORTEP diagram.

FIGS. 3, 4, 5 and 6 are the infrared spectra of the compounds produced in Examples 1, 2, 16 and 17, respectively.

DETAILED DESCRIPTION

Figure 1:
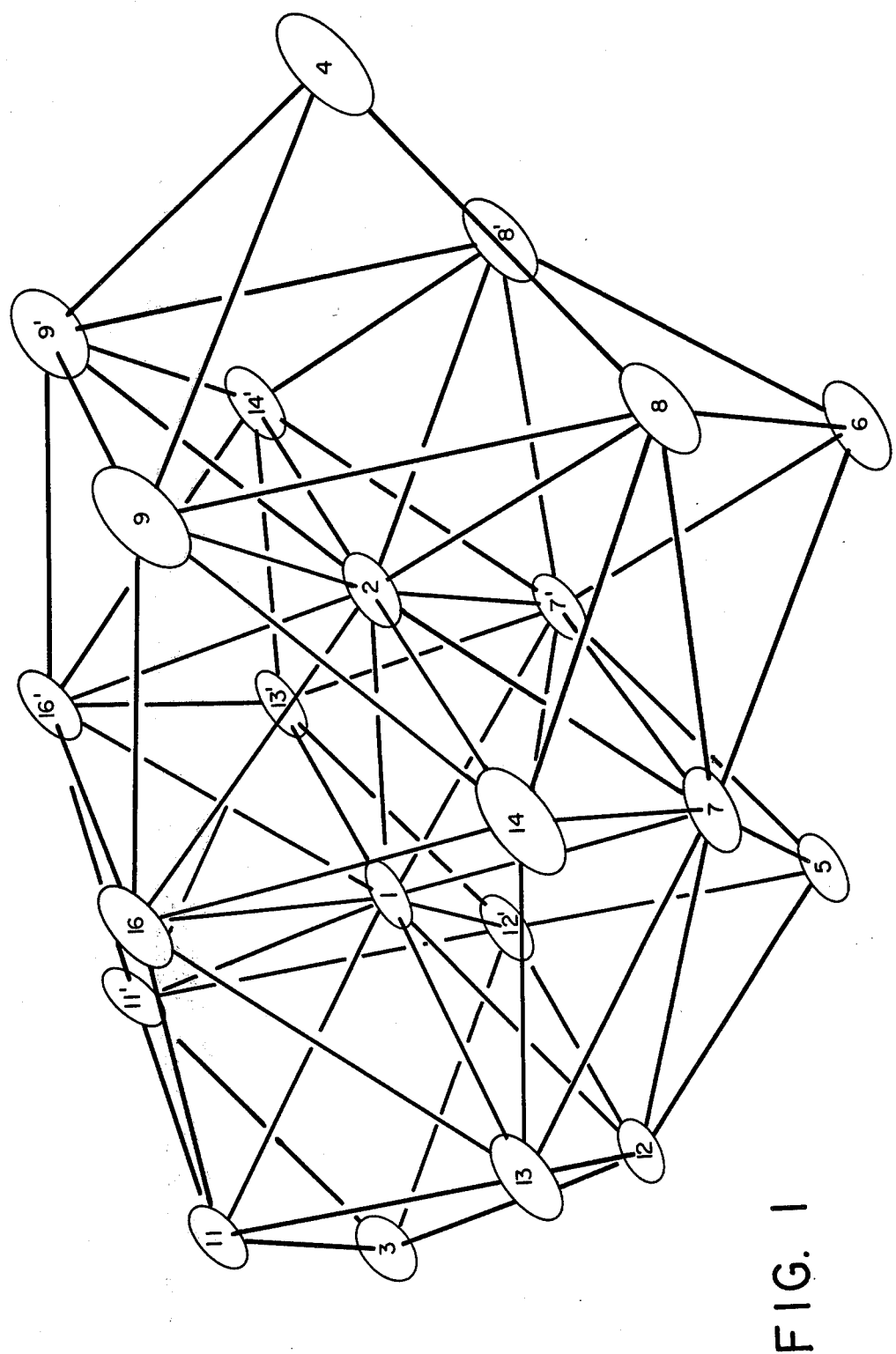
FIGS. 1 through 6 of the accompanying drawings are discussed in detail in the context of Examples 1, 2, 16 and 17 set forth hereinbelow.

To facilitate discussion, the Rh-22 carbonyl cluster compounds of the present invention may, in a preferred embodiment, be depicted by the following empirical formula I:

$$[Rh_{22}(CO)_yH_x][M]_n \qquad (I)$$

wherein M is a cation, y usually has a value from about 33 to about 44, x is zero or a positive number having an average value of up to about 10 and is usually at least one, and n corresponds to the charge of the [Rh$_{22}$(CO)$_y$H$_x$] cluster. When n is zero, the cluster are neutral compounds, [Rh$_{22}$(CO)$_y$H$_x$]°. On the other hand, when n is other than zero, the compounds are salts and the anionic rhodium carbonyl cluster portion, [Rh$_{22}$(CO)$_y$H$_x$]$^{n-}$, is a mono- di-, tri-, tetra-, penta-, etc. anion, depending, of course, on the value of n.

In the salt clusters of the present invention, the anionic docosarhodium carbonyl cluster is in association with a cation (i.e., "M" of Formula I) which can be inorganic or organic, or an inoganic/organic complex ion. Illustrative of suitable inorganic cations are: the ammonium cation, NH$_4$+; any of the alkali metal cations (e.g., Li+, N+a, K+, Rb+ and Cs+); any of the alkaline earth metal cations (e.g., Ca++, Mg++); cations of transition metals (e.g., iron, cobalt and iridium cations); and other metal cations such as, for example, aluminum, zinc, chromium, and zirconium cations. Among the classes of suitable organic cations encompassed "M" of Formula I are: quaternary ammonium cations, (R°)$_4$N+; quaternary phosphonium cations, (R°)$_4$P+; and bis (triorgano phosphine) iminium cations, [(R°)$_3$P]$_2$N+; wherein R° in these cations is an organic radical. Also encompassed by "M" of Formula I are cation-containing hetero-macrocyclic complexes wherein the hetero-macrocyclic portion is a crown ether or cryptand, and the cation which is in complex combination with the hetero-macrocyclic compound is a metal cation, usually an alkali metal cation.

Suitable quaternary ammonium cations, quaternary phosphonium cations and bis (triorgano phosphine) iminium cations with which the anionic rhodium carbonyl clusters of the invention may be associated include those of respective Formulas II, III and IV:

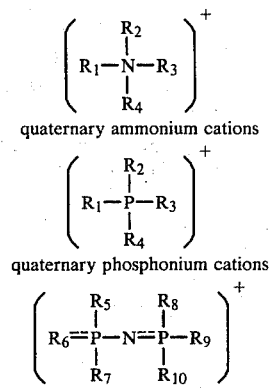

quaternary ammonium cations (II)

quaternary phosphonium cations (III)

(IV)

bis (triorgano phosphine) iminium cations wherein $R_1$ through $R_4$ of Formulas II and III, and $R_5$ through $R_{10}$ of Formula IV, can be any of the following groups: alkyl, including straight and branched chain alkyls, having from 1 to 20 and usually no more than 12, carbon atoms such as, for example, methyl, ethyl, n-propyl, isopropyl, n-butyl, octyl, 2-ethylhexyl and dodecyl; cycloaliphatic groups, including monocyclic and bicyclic groups, having from 5 up to 12 carbon atoms such as, for example, cyclopentyl, cyclohexyl and bicyclo [2.2.1] heptyl groups; aromatically unsaturated groups, including aryl, alkaryl and aralkyl, having from 6 up to 20 carbon atoms such as, for example, phenyl, naphthyl, xylyl, tolyl, t-butylphenyl, benzyl, beta-phenylethyl and 3-phenylpropyl; functionally substituted alkyls such as alkyls encompassed by $R_1$ through $R_{10}$ which are substituted with hydroxy, alkoxy or aryloxy groups such as, for example, beta-hydroxyethyl, ethoxymethyl and phenoxyethyl; and polyalkylene ether groups of the formula $(C_pH_{2p}O)_q$-OR' where p has an average value from 1 to 4, g has an average value from 2 to about 150, and R' is hydrogen or alkyl of 1 to 12 carbon atoms. Illustrative of such polyalkylene ether groups are: poly(oxyethylene), poly(oxypropylene), poly(oxyethyleneoxypropylene) and poly(oxyethylene-oxybutylene). It is to be understood that the respective sets of $R_1$ through $R_4$ groups of Formulas II and III may be the same as or different from one another. Likewise, the $R_5$ through $R_{10}$ groups of Formula IV may be the same as or different from one another.

The rhodium carbonyl clusters of this invention are formed by the coupling of mononuclear rhodium compounds or the comdensation of polynuclear rhodium compounds under condition of temperature and CO pressure, in the presence of solubilizing counterions, such that the desired $Rh_{22}$ cluster is formed. The process is a compromise of conditions to maximize the formation of this cluster. For example, many rhodium compounds can provide the rhodium source yielding the desired product. Illustrative of these are:

$Rh(CO)_2AcAc*$, $Rh_4(CO)_{12}$, $Rh_6(CO)_{16}$, $Rh_7(CO)_{16}{}^{3-}$, $Rh_{12}(CO)_{30}{}^{2-}$, $Rh_{14}(CO)_{25}{}^{4-}$, $Rh_{15}(CO)_{27}{}^{3-}$,

*rhodium dicarbonylacetylacetonate and mixtures of these. Obviously the choice of the rhodium source will affect the process mix. In some cases, it will be preferred to combine a mononuclear species, such as $Rh(CO)_2AcAc$, with a polynuclear compound, such as $R_{15}(CO)_{27}{}^{3-}$. The combination of rhodium compounds which one selects should be predicated on their capability to equilibrate to a $Rh_{22}$ cluster. The growth of a cluster from a mononuclear species or the condensation from at least one polynuclear specie is controlled by the ability to solubilize such, in the first instance, and achieve a solubilized $Rh_{22}$ cluster, in the last instance. Between such instances is the role played by temperature and CO pressure to maximize the production of the desired cluster. The higher the temperature that one employs the faster and larger is cluster formation; size being eventually determined by time of reaction under the established reaction conditions. However, CO pressure serves to shortstop cluster growth by providing CO bonded to Rh atoms with growth sites. Less CO pressure favors cluster aggregation or growth while excessively high CO pressure retards growth altogether and can result in cluster fragmentation, assuming the presence of clusters in the first instance.

With such comprehension of the path to cluster formation, the general procedure to $Rh_{22}$ cluster formation becomes readily apparent. In the first step of the process, Rh, either as a soluble mononuclear or polynuclear compound, is dissolved in a solvent in the presence of a solubilizing agent, preferably one which provides counterions to the intermediate species being assembled into the formation of the desired $Rh_{22}$ product. The most favorable solubilizing agent is one which provides monovalent counterions. Polyvalent counterions tend to generate insolubilization of intermediate species and such prevents formation of the desired product.

The monovalent counterion comprises the combination of a monovalent anion and cation. In most instances the monovalent cation is an alkali metal. The monovalent anion is any reducing basic medium for the initial hydrogenation of the rhodium souce material used to form the desired $R_{22}$ cluster compound. The anion can be, e.g., hydroxy, carbonate, bicarbonate, sulfate and carboxylate.

Alkali metal salts, preferably alkali metal salts of monocarboxylic acids, are desirable solubilizing agents. Their choice is dependent upon the solvent used in the process. The solvent of choice is one which dissolves the rhodium source compound, the formed intermediates and the $Rh_{22}$ cluster product. Many solvents are suitably employable in this process.

Illustrative solvents which are generally suitable in making the homeogeneous mixture include, for example, ethers such as tetrahydrofuran, tetrahydropyran, diethyl ether, such as tetrahydrofuran, tetrahydropyran, diethyl ether, 1,2-dimethoxybenzene, 1,2-diethoxybenzene, the mono-and dialkyl ethers of ethers of ethylene glycol, of propylene glycol, of butylene glycol, of diethylene glycol, of butylene glycol, of diethylene glycol, of dipropylene glycol, of triethylene glycol, of tetraethylene glycol, of dibutylene glycol, of oxyethylenepropylene glycol, etc; alkanols such as methanol, ethanol, propanol, isobutanol, 2-ethylhexanol, etc.; ketones such as acetone, methyl ethyl ketone, cyclohexanone, cyclopantanone, etc.; esters such as methyl acetate, ethyl acetate, propyl acetate, butyl acetate, methyl propionate, ethyl butyrate, methyl laurate etc.; water; gamma-butyrolactone, deltavalerolactone; substituted and unsubstituted tetrahydrothiophene-1,1-dioxides (sulfolanes) as disclosed in U.S. application Ser. No. 537,885, filed on Jan. 2, 1975. These include sulfolanes of the formula:

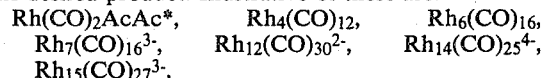

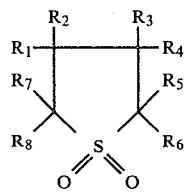

wherein each of $R_1$ through $R_8$ is at least one of hydrogen; hydroxyl; straight or branched chain alkyl, preferably having from 1 to 12 carbon atoms, preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo [2.2.1] heptl and the like; or an aryl, alkyl-aryl, or aralkyl group such as phenyl, naphthyl, xylyl, tolyl, benzyl, beta-phenylethyl and the like; an ether of the formula (O—R°) wherein R° may be aryl or lower alkyl having from 1 to 12 carbon atoms, preferably 1 to 4 carbon atoms in the alkyl chain; an alkylene or polyalkylene ether of the formula $-(OC_nH_{2n})_x\text{-OR}^{\circ\circ}$ wherein n has an average value of from 1 to about 4, x has an average value of from 1 to about 150, preferably 1 to about 20, most preferably 1 to about 4, and $R^{\circ\circ}$ may be hydrogen or alkyl having from 1 to 6 carbon atoms in the alkyl chain, such as poly(oxyethylene), poly(oxyethyleneoxypropylene), alkylene and polyalkylene glycols and lower alkyl ethers thereof; a carboxylate group of the formula:

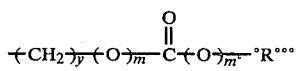

wherein y may have value between 0 and 12, m and m° may be zero or one provided that when either m or m° is one the other is zero, and $R^{\circ\circ\circ}$ may be a lower alkyl group having from 1 to 12 carbon atoms, preferably from 1 to 4 carbon atoms, or aryl, and the like.

Also, the crown ethers are suitable herein, particularly those as described in U.S. Pat. No. 4,162,261 to L. Kaplan, patented July 24, 1979, which is incorporated by reference herein.

The crown ethers contain in the principle ring at least 4 oxygen atoms each separated from the other by at least two aliphatic carbon atoms in series. The principal ring contains at least two ring oxygen atoms which are each joined to ethylene or substituted ethylene groups. The remainder of the principal ring oxygen atoms are joined to either trimethylene, tetramethylene, substituted trimethylene, or substituted tetramethylene groups, or mixtures of them. The maximum number of ring oxygen atoms in the principal ring may be as much as about 100, however, it is desirable that those ring oxygen atoms joined to groups other than ethylene or substituted ethylene number not more than about 50 when the number of such ring oxygen atoms exceeds about 52.

These crown ethers include [18]-crown-6 and [15]-crown-5.

Particularly desirable solvents are tetraglyme, sulfolane, gamma-butyrolacetone and the crown ethers. Other very desirable solvents include mixtures of tetraglyme and sulfolane, mixtures of sulfolane and butyrolactone, mixtures of crown ethers and sulfolane, mixtures of crown ethers and tetraglyme mixtures of crown ethers and butyrolactone, and mixtures of tetraglyme and butyrolactone.

The molar ratio of the solubilizing agent to the Rh compound providing the rhodium source is typically from about 2-5 to 1. The temperature of the reaction can be coordinated with the CO pressure applied. The higher the CO pressure the lower the temperature required and vice versus. Temperatures of from about 100° C. to about 250° C. are contemplated, though higher and lower temperatures are also within the purview of this invention. A preferred temperature range is between about 125° C. to about 175° C., and a most preferred range is between about 140° to about 160° C. The CO pressure can range from 0.1 atmosphere, or lower, to about 1000 atmospheres, or higher. A desirable CO pressure is between about 0.25 atmospheres and about 300 atmospheres. In the typical case, atmospheric pressures will be favored.

The amount of the rhodium source compound employed in the process is not narrowly critical. An amount of such compound which is soluble in the solvent of choice is desirable. Typically that amount ranges from about 0.01 weight percent to about 20 weight percent basis weight of the solution. Preferably that it is between about 0.1 weight percent to about 10 weight percent, same basis.

The rhodium carbonyl cluster compounds of the compounds of the present invention are effective catalysts in a variety of processes including, for example, the processes described in aforementioned U.S. Pat. Nos. 3,833,634 and 4,133,776 for the production of polyhydric alcohols such as ethylene glycol by the reaction of oxides of carbon and hydrogen (synthesis gas).

In accordance with the present invention, the reaction of hydrogen and carbon monoxide in the presence of the rhodium carbonyl complex catalyst of the present invention at broadly speaking, temperatures between about 100° C. and about 375° C. and a pressure of between about 500 and 50,000 pounds per square inch (p.s.i.a.) effectively produce polyfunctional oxygen-containing compounds such as polyhydric alcohols and their ester derivatives. Key products are ethylene glycol and ethylene diacetate. Other products are monohydric alcohols such as methanol and ethanol, and their ether and ester derivatives.

As described in the above noted patents, the reaction is preferably conducted in a homogeneous liquid phase so that the rhodium-containing catalyst and even the products of reaction are in solution. The solution typically requires the presence of a solvent, one function of which is to keep the catalyst in solubilized form before, during, and after the reaction. Illustrative of suitable solvents are those disclosed for example, in U.S. Pat. Nos. 3,833,634, 3,957,857, 3,968,136, 4,111,975, 4,162,261, and in U.S. applications Ser. No. 537,885, filed on Jan. 2, 1975 and Ser. No. 618,021, filed on Sep. 20, 1975.

Moreover, the process is carried out in the pressure of one or more ligands selected from among groups referred to in the patent literature as organic oxygen ligands, organic nitrogen ligands and organic azaoxy ligands.

The rhodium carbonyl complex cluster of the invention may be preformed and added to the reaction solution as such or it may be formed in situ. For example, the rhodium carbonyl complexes can be generated in situ by providing carbon monoxide to the reaction solution.

A distinct advantage of using the rhodium carbonyl complex clusters of this invention as a catalyst for the production of polyhydric alcohols by the homogeneous catalytic reaction of synthesis gas is the simplification of operations involved in preparing the catalyst. The composition of the Rh 22 cluster composition, as prepared, provides are optimum value, for example, of the Cs/Rh atom ratio (eg 0.22–0.23) such as required in starting with Rh(CO)$_2$(AcAc). As is known, heretofore the ratio has to be adjusted by the addition of alkali metal salts such as cesium carboxylates during catalyst preparation. The required ratio, however, is already present in the Rh 22 cluster complex, which results in a catalyst system of the same activity as would be obtained from, for example, Rh(CO$_2$)AcAc-cesium carboxylate mixtures, ethers eliminating the need to add salts and the possibility of errors during catalyst preparation.

Although this invention has been described with respect to a number of details, it is not intended that this invention should be limited thereby. Moreover, the examples which follow are intended solely to illustrate a variety of, including the most favorable, embodiments of this invention and are not intended in any way to limit the scope and the intent of this invention.

EXAMPLE 1

Preparation and Crystallographic Study of the [Cs/18-crown-6]$^+$ Salt of [Rh$_{22}$(CO)$_{35}$H$_x$]$^{n-}$

(A) Preparation

Figure 3:
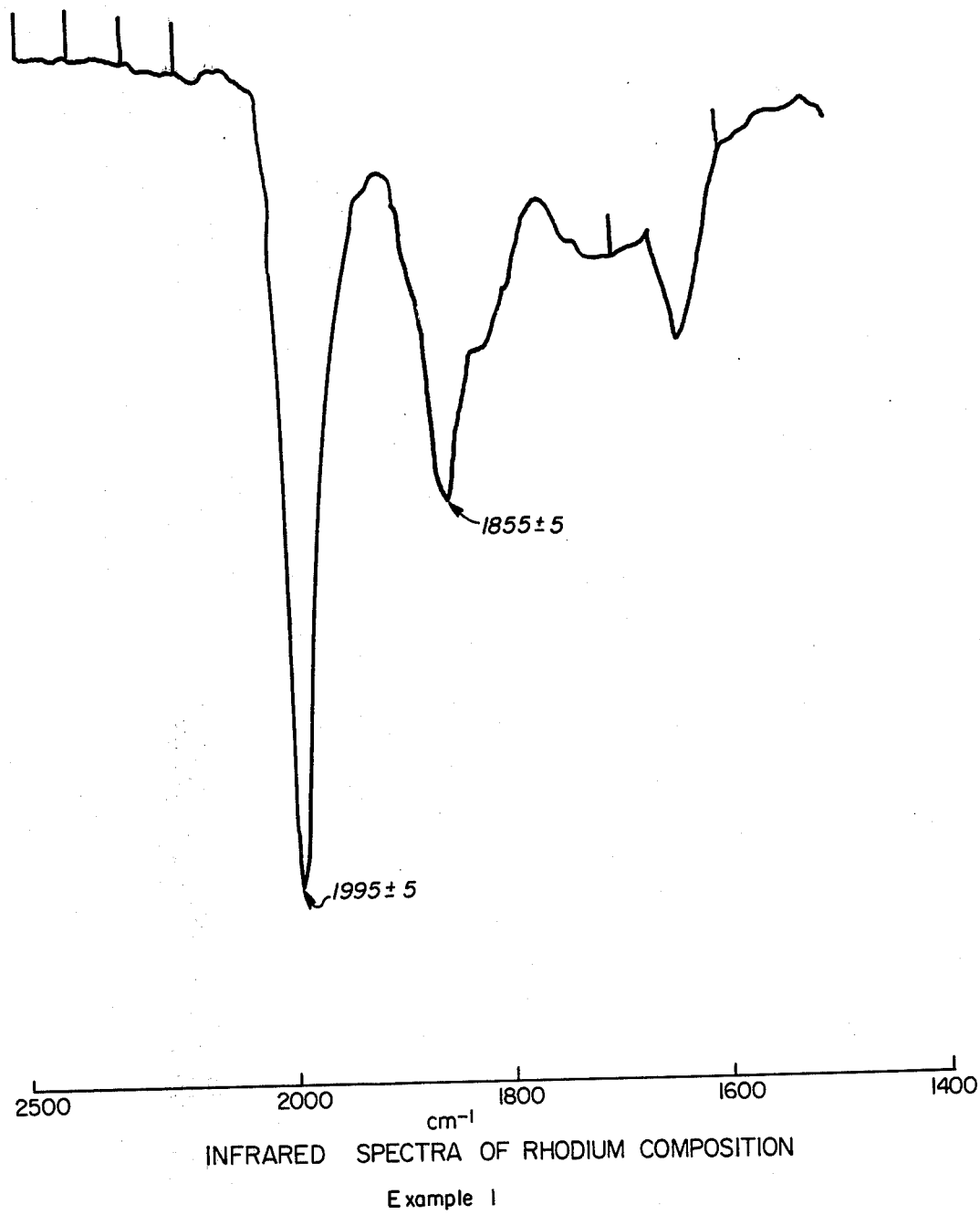

After melting 77.280 grams of 18-crown-6 contained in a carbon monoxide-purged Schlenck tube, and degassing and sparging with carbon monoxide, there were added thereto: rhodium dicarbonylacetylacetonate (3.1304 grams) and cesium benzoate (0.7096 gram) dissolved in 6.72 grams of water. While sparing continuously with carbon monoxide at atmospheric pressure, the temperature was raised to and maintained at about 150° C. for about 20 hours. After this period of time, the solids which had formed were separated by filtration through a hot-jacketed Schlenk filter. The solids were washed numerous times with dry isopropanol until the filtrate was colorless. The washed solids were dried under high vacuum and were then extracted with about 250 ml. of tetrahydrofuran ("THF"). Upon stripping the extract to about one-third of its THF content, solids precipitated. After extracting the solids with THF, the filtrate was stripped of solvent and the solids were recovered. The solids were dissolved in acetone. A sample of the resulting solution was subjected to infrared analysis; the infrared spectral pattern is shown in FIG. 3 and, as shown, exhibits a wavelength band of strong intensity at about 1995 ±5 cm$^{-1}$ and a band of medium intensity at about 1855 ±5 cm$^{-1}$.

Single crystals suitable for X-ray diffraction structural studies were prepared using slow solvent diffusion techniques using the acetone solution in combination with isopentane, and acetone/18-crown-6/isopentane mixtures.

(B) Structural Determinations Based on Crystallographic Analysis

The crystallographic study of a single crystal of the cluster compound produced in accordance with Part (A) of this example showed the presence of four clusters and eighteen cesium/18-crown-6 cations per unit cell, and an overall empirical formula for the unit cell of:

$$Cs_{18}Rh_{88}O_{308}C_{476}H_{672}$$

Therefore, the average empirical formula of each cluster in the unit cell is $$Cs_{4.5}Rh_{22}O_{77}C_{119}H_{168}$$

which in turn corresponds to a structural formula for the cluster of:

$$[Cs_{4.5}(C_{12}H_{24}O_6)_7],[Rh_{22}(CO)_{35}].$$

The ratio of 4.5 cesium cations per cluster indicates that the negative charged of the docosarhodium pentatriacontacarbonyl cluster is 4.5 and that the final stoichiometry of the structure is:

$$[Cs_9(C_{12}H_{24}O_6)_{14}],[Rh_{22}(CO)_{35}H_x]_2.$$

This anomaly of a negative charge of minus 4.5 is apparently not due to the presence of other cationic species such as hydronium ions (i.e., H$_3$O$^{30}$) which were not found in the final structural data. A probable explanation for the indicated average negative charge of minus 4.5 is the presence in the unit cell of equimolar amounts of [Rh$_{22}$(CO)$_{35}$H$_{x+1}$]$^{4-}$ and [Rh$_{22}$(CO)$_{35}$H$_x$]$^{5-}$. This explanation is consistent with the presence of shoulders on the infrared band usually assigned to the absorption corresponding to bridging carbonyl ligands (1860, 1850, 1845 cm$^{-1}$). That is, the presence in the unit cell of two clusters, each with degrees of reduction of −4 and −5 respectively, should originate two different bridging carbonyl infrared absorptions. (1995±5 cm$^{-1}$) actually, however, only one terminal carbonyl infrared absorption was detected.

This could be a consequence of the lack of resolution of two distinct terminal bands, or could results from an effective coincidence in the frequency of the infrared absorption for the terminal ligands of the aforementioned respective tetravalent and pentavalent anionic cluster species. Further, the presence of only one detectable terminal carbon monoxide infrared absorption could be due to the tendency of the large clusters size to minimize any affect that a change in the degree of reduction might otherwise have on infrared absorption. The presence of a variable number of protons in the species of the docosarhodium pentatriacontacarbonyl cluster anions affects the degree of reduction. Although the presence of such protons could not be confirmed by nuclear magnetic resonance or other spectroscopic techniques, their presence is required to explain the existence of two docosarhodium pentatriacontacarbonyl clusters with different degrees reduction.

The cesium cations of the cluster compound subjected to the crystallographic study are present in the unit cell as 18-crown-6 solvates. In the aforementioned stoichiometric structure, it is seen that the Cs:18-crown-6 ratio is 9:14, corresponding to an average of about 1.55 cesium atoms per molecule of crown ether. This average value indicates the presence of the three cationic species [Cs(18-crown-6)$_2$]$^+$, [Cs(18-crown-6]$^+$, and [Cs$_2$(18-crown-6)$_3$]$^{2+}$, with three cesium atoms forming the first type of complex, two forming the second type and four cesium atoms coordinated as in the latter complex.

(C) Molecular Model of the "RH$_{22}$" Cluster

FIG. 1 is a view of the rhodium skeleton of the molecular mode of the illustrative docosarhodium pentatriacontacarbonyl cluster compound of this example. This molecular model is based on a computer-controlled operation using the atomic coordinates supplied by the computer used in the above-described crystallographic study of a single crystal of the compound. Schematic FIG. 2 is a view of the model taken parallel to the symmetry plane, o$_1$.

Figure 2:
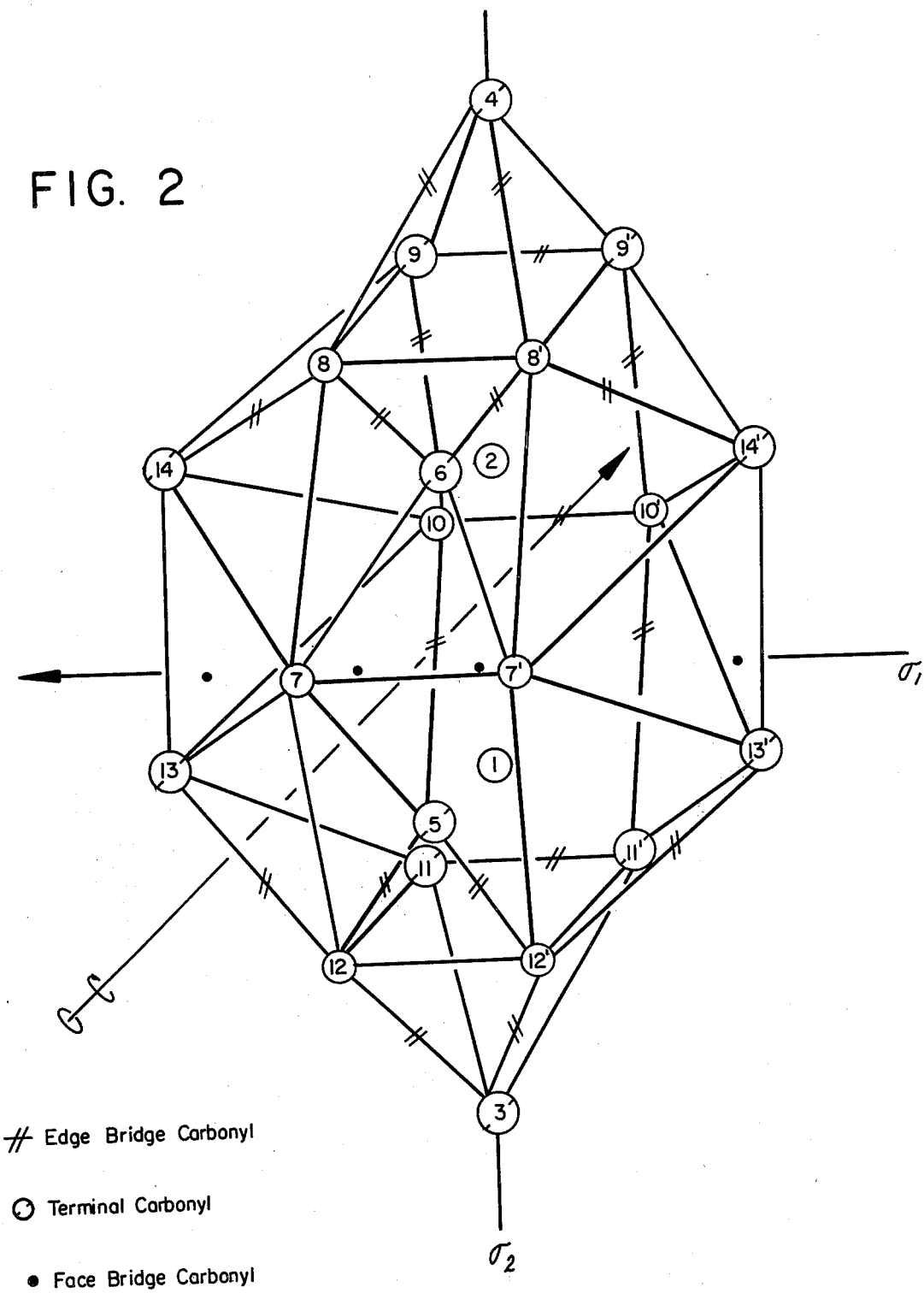

As best shown in FIG. 2, the twenty-two rhodium atom skeleton comprises three slightly distorted rectangular and elapsed rhodium layers with rhodium atoms (7, 8, 9, 10, 11, 12) at the corners of each layer, these rhodium atoms being related to their respective images (7', 8', 9', 10', 11', 12') by a mirror plane. There are two apical rhodium atoms (3, 4) capping the two rectangular basal faces (11—11'-12—12'; 8—8'-9—9'). As shown in FIGS. 1 and 2, these apical rhodium atoms are located trans to each other on the longer axis of the cluster. Two other rhodium atoms (1, 2) are located on this longer axis, each being positioned within the respective cavities defined by the aforementioned three rhodium layers. The longest axis of the cluster is thus defined by the two apical rhodium atoms (3, 4) and the two encapsulated rhodium atoms (1, 2). In addition to the aforementioned two basal faces, the surface of the cluster has eight other rectangular faces. These eight additional faces are defined by the aforementioned three rectangular rhodium layers.

Six of these eight additional faces are capped by rhodium atoms (5, 6, 13, 13', 14 14'), thereby accounting for the remaining six rhodium atoms. Two of these rhodium atoms (5, 6) constitute a unique capping couple in the sense that these two rhodium atoms are farther apart than those in the two remaining capping couples (13—13', 14—14'). There are six distorted rectangular faces capped by rhodium atoms 13, 13', 14 and 14'. The two remaining faces (9, 9'; 10, 10', 11, 11') of the cluster's faces are square and uncapped and, as best shown in FIG. 1, have a common edge (10—10').

The distribution of the thirty-five carbonyl ligands coordinated with the rhodium skeleton of the cluster compound is shown in FIG. 2 and is as follows: twelve terminal, nineteen edge-bridging, and four face-bridging ligands.

EXAMPLE 2

Further Synthesis of Cesium/Crown Ether Salt of [Rh$_{22}$(CO)$_{35}$H$_x$]n—

Figure 4:
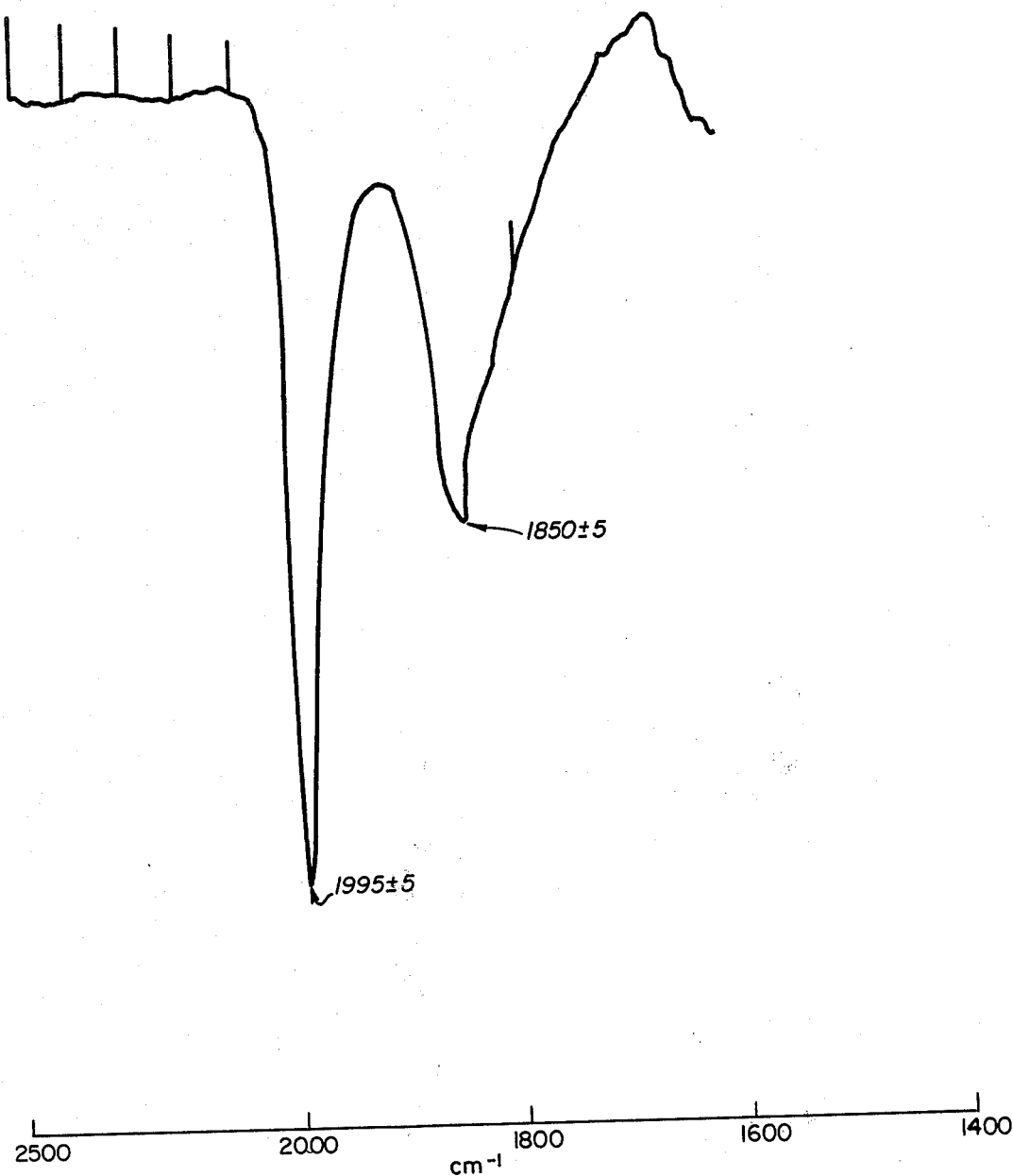

To a 500 ml. capacity round bottom flask equipped with a stirrer and sparger there were added 308.0 grams of 18-crown-6. The crown ether was heated to about 70° C. and saturated with carbon monoxide by means of the sparger. The crown ether was maintained under these conditions while charging thereto: rhodium dicarbonylacetylacetonate (12.43 grams; 48.94 mmoles) and cesium benzoate (3.84 grams; 12.89 mmoles) dissolved in 26.8 grams of water. The mixture was heated up to about 150° C. and maintained at this temperature for about 17 hours while being sparged with carbon monoxide at atmospheric pressure. After this period of time, the solution (containing some solids) was allowed to cool to about 80° C. and was then rapidly charged to a large excess of freshly dry isopropanol. Precipitation occurred almost immediately. The solids were collected by filtration under argon using a Schlenk filter, washed several times with isopropanol, and dried under vacuum. The dried solids weighted 13.23 grams corresponding to a yield of 88.3% of the cesium/18-crown-6 salt of ]Rh$_{22}$(CO)$_{35}$H$_x$]$^{n-}$, the said yield being based on the amount of initially charged rhodium. Elemental analysis by atomic absorption spectroscopy of solutions of this material in sulfolane showed the presence of 8035.71 ppm rhodium and 1708.07 ppm cesium, corresponding to a Rh/Cs atom ratio of 6.0. Fig. 4 is the infrared spectral pattern of this cluster salt (dissolved in acetone) and, as shown, is characterized by a wavelength band of strong intensity at about 1995 ±5 cm$^{-1}$ and a band of medium intensity at about 1850 ±5 cm$^{-1}$, with shoulders at 1855 ±5 cm$^{-1}$.

EXAMPLES 3 to 15

The purpose of these examples is to illustrate the use of the docosarhodium carbonyl cluster compounds of this invention as catalysts for the conversion of carbon monoxide and hydrogen to oxygen-containing compounds with the advantage that it allows the preparation of catalyst systems usefull for the conversion of CO/H$_2$ into polyalcohols that have the Cs:Rh atomic ratios required for optimum catalyst's properties without having to add additional components such as alkali salts e.g. cesium benzoate, to adjust the aforementioned ratio, as required when catalysts based on Rh(CO)$_2$ acac are used.

These reactions were effected in a 150 ml. capacity stainless steel reactor capable of withstanding pressures up to 7000 atmospheres. In each example, the reactor was charged with a premix (prepared under an argon atmosphere) of: the cesium/crown ether salt of the rhodium carbonyl cluster prepared in accordance with Example 2 above, 75 ml. of sulfolane solvent, and N-methylmorpholine in the amount specified below. The reactor was sealed and charged with a gaseous mixture containing equal molar amounts of carbon monoxide and hydrogen to a pressure as specified below. Heat was applied to the reactor and its contents; when the temperature of the mixture inside the reactor reached the designated reaction temperature recited below, as measure by a suitably placed thermocouple, addition of carbon monoxide and hydrogen (H$_2$/CO=1) was made to bring the pressure to the specified reaction pressure recited below. The amount of N-methylmorpholine amine promoter, as well as the temperatures and pressures maintained in these examples, were as indicated in Table I below.

After the reaction was terminated, the vessel and its contents were cooled to room temperature, the excess gas vented, and the reaction product mixture removed. Analysis of the reaction product mixture was made by gas chromatographic analysis using a Hewlett Packard FM TM model 810 Research Chromatograph. Results of the analysis of the product mixture in terms of ethylene glycol ("glycol") and methanol ("MeOH") are given in Table I.

Rhodium recovery was determined by atomic absorption analysis of the contents of the reactor after the venting of the unreacted gases at the end of the reaction. The rhodium recovery values may be characterized as the percent rhodium based on the total rhodium charged to the reactor that is soluble or suspended in the reaction mixture after the specified reaction time. These values are also given in Table I which follows.

TABLE I

USE OF Cs/18-CROWN-6 SALT OF $[Rh_{22}(CO)_{35}H_x]^n$ TO PRODUCE GLYCOL FROM SYNTHESIS GAS[a]

| Ex. | Amine Promoter, NMM[b] (mmole) Actual | Scaled[d] | Rh Concentration[c] (ppm.) Initial | Final | Temp., °C. | Pressure (psig) | Rate[d] (M hr$^{-1}$) to MeOH | Glycol | % Rh Recovered[e] |
|---|---|---|---|---|---|---|---|---|---|
| 3 | 10 | 16.4 | 1825 | 1449 | 270 | 15,000 | 3.48 | 4.03 | 79 |
| 4 | 10 | 16.4 | 1825 | 1489 | 260 | 15,000 | 2.38 | 2.77 | 82 |
| 5 | 10 | 16.4 | 1825 | 1590 | 250 | 15,000 | 1.48 | 1.66 | 87 |
| 6 | 10 | 8.2 | 3655 | 2952 | 260 | 12,500 | 3.04 | 2.35 | 81 |
| 7 | 10 | 8.2 | 3655 | 2907 | 250 | 12,500 | 1.84 | 1.33 | 80 |
| 8 | 10 | 8.2 | 3655 | 3097 | 240 | 12,500 | 1.58 | 0.88 | 85 |
| 9 | 10 | 8.2 | 3655 | 2529 | 260 | 8,000 | 0.43 | 0.28 | 69 |
| 10 | 2.0 | 2.7 | 2208 | 1554 | 260 | 12,500 | 1.97 | 1.96 | 70 |
| 11 | 4.0 | 5.4 | 2208 | 1673 | 260 | 12,500 | 1.97 | 2.07 | 76 |
| 12 | 6.0 | 8.1 | 2208 | 1699 | 260 | 12,500 | 2.01 | 2.08 | 77 |
| 13 | 2.0 | 2.7 | 2208 | 1519 | 270 | 15,000 | 4.62 | 3.33 | 69 |
| 14 | 4.0 | 5.4 | 2208 | 1570 | 270 | 15,000 | 5.09 | 4.01 | 72 |
| 15 | 6.0 | 8.1 | 2208 | 1700 | 270 | 15,000 | 6.28 | 4.03 | 77 |

[a] In each example, the solvent was sulfolane (75 ml.) and the $H_2$/CO ratio was 1/1.
[b] N-Methylmorpholine.
[c] The rhodium source was the Cs/18-crown-6 salt of the "$Rh_{22}$" carbonyl cluster prepared in accordance with Example 2.
[d] Scaled proportionately to 3000 ppm. rhodium using the conversion factors 1.64, 0.82 and 1.36 for the 1825, 3635 and 2208 ppm. rhodium systems, respectively.
[e] % rhodium recoveries are based on the actual Rh concentrations at the beginning and the end of the respective examples and are uncorrected for dilution by the products.

Set forth in Table II hereinbelow are further experiments, designated Runs 1 through 17, which were performed in the manner described with specific reference to the examples of Table I with the following exceptions: rhodium dicarbonylacetylacetonate was used as the rhodium source in place of the cesium/crown ether salt of the docosarhodium pentatriacontacarbonyl cluster prepared in accordance with Example 2, and cesium benzoate was used in all but the last two runs. The rhodium concentration of the reaction mixture, the amount of N-methylmorpholine and cesium benzoate promoters, the reaction temperatures and pressures, and the results of these runs are included in Table II which follows:

about 17 hours. The solids which formed were separated by filtration through a heated Schlenck filter. The filtered solids were washed several times with distilled THF, and were then dissolved through the filter with dry acetone. After standing overnight, a sample of the acetone solution was subjected to infrared analysis; the infrared spectral pattern showed wavelength bands only a 1990±5 cm$^{-1}$ and 1850±5 cm$^{-1}$, consistent with the characteristic bands for the cesium/crown ether salt of the Rh-22 carbonyl cluster described under Examples 1 and 2. The acetone solution was then combined with about 4 times its volume of an isopropanol solution of (triphenylphosphine) iminium chloride, $[(C_6H_5)_3P]_2NCl$ containing about 1 gram of the chlo-

TABLE II

USE OF CATALYST SYSTEMS BASED ON $Rh(CO)_2AcAc$ TO PRODUCE GLYCOL FROM SYNTHESIS GAS[a]

| Run. | Amine Promoter NMM[b] (mmole) Actual | Scaled[e] | Salt Promoter $PhCO_2Cs^c$ (mmole) Actual | Scaled[e] | Rh Concentration[d] (ppm.) Initial | Final | Temp., °C. | Pressure (psig) | Rate[e], M hr$^{-1}$ to MeOH | Glycol | % Rh Recovered[f] |
|---|---|---|---|---|---|---|---|---|---|---|---|
| 1 | 10 | 18.5 | 0.33 | 0.61 | 1625 | 1173 | 270 | 15,000 | 1.11 | 1.29 | 72 |
| 2 | 10 | 18.5 | 0.43 | 0.79 | 1625 | 1155 | 270 | 15,000 | 3.88 | 3.51 | 71 |
| 3 | 10 | 18.5 | 0.25 | 0.46 | 1625 | 1115 | 270 | 15,000 | 2.40 | 2.77 | 69 |
| 4 | 10 | 18.5 | 0.33 | 0.61 | 1625 | 1205 | 260 | 15,000 | 0.92 | 1.29 | 74 |
| 5 | 10 | 18.5 | 0.43 | 0.79 | 1625 | 1275 | 260 | 15,000 | 0.74 | 1.11 | 78 |
| 6 | 10 | 18.5 | 0.25 | 0.46 | 1625 | 1208 | 260 | 15,000 | 1.11 | 1.48 | 74 |
| 7 | 4.3 | 7.9 | 0.25 | 0.46 | 1625 | 1388 | 270 | 15,000 | 5.13 | 6.35 | 85 |
| 8 | 4.3 | 7.9 | 0.33 | 0.61 | 1625 | 1185 | 270 | 15,000 | 3.67 | 4.65 | 73 |
| 9 | 4.3 | 7.9 | 0.43 | 0.79 | 1625 | 1205 | 270 | 15,000 | 4.82 | 5.78 | 74 |
| 10 | 10 | 18.5 | 0.33 | 0.61 | 1625 | 1239 | 260 | 12,500 | 0.92 | 0.92 | 76 |
| 11 | 10 | 18.5 | 0.43 | 0.79 | 1625 | 1253 | 260 | 12,500 | 1.11 | 1.11 | 77 |
| 12 | 10 | 18.5 | 0.25 | 0.46 | 1625 | 1294 | 260 | 12,500 | 1.11 | 1.11 | 80 |
| 13 | 10 | 18.5 | 0.33 | 0.61 | 1625 | 1201 | 250 | 12,500 | 1.11 | 1.11 | 74 |
| 14 | 10 | 18.5 | 0.43 | 0.79 | 1625 | 1206 | 250 | 12,500 | 1.11 | 1.11 | 74 |
| 15 | 10 | 18.5 | 0.25 | 0.46 | 1625 | 1182 | 250 | 12,500 | 1.11 | 1.11 | 73 |
| 16 | 5.0 | 4.6 | None | — | 3250 | 2265 | 240 | 8,000 | 0.36 | 0.30 | 70 |
| 17 | 5.0 | 4.6 | None | — | 3250 | 2246 | 240 | 8,000 | 0.37 | 0.30 | 69 |

[a] In each example, the solvent was sulfolane (75 ml.) and the $H_2$/CO ratio was 1/1.
[b] N-Methylmorpholine.
[c] Cesium benzoate.
[d] The rhodium source was rhodium dicarbonylacetylacetonate.
[e] Scaled proportionately to 3000 ppm. rhodium using the conversion factors 1.846 and 0.92 for the 1625 and 3250 ppm. rhodium systems, respectively.
[f] % rhodium recoveries are based on the actual Rh concentrations at the beginning and at the end of the respective runs, and are uncorrected for dilution by the products.

EXAMPLE 16

Preparation of the Bis (triphenylphosphine) iminium Salt of Rh-22 Carbonyl Cluster Anion The following were charged under carbon monoxide to a Schlen tube immersed in an oil bath: 18-crown-6 (77.28 grams), rhodium dicarbonylacetonate (3.1304 grams) and cesium benzoate trihydrate (0.7096 grams) dissolved in 6.72 grams of water. While stirring the solution and sparging carbon monoxide below the liquid level, the temperature was held at 150°-155° C. for ride in 15 ml. of solvent.

Figure 5:
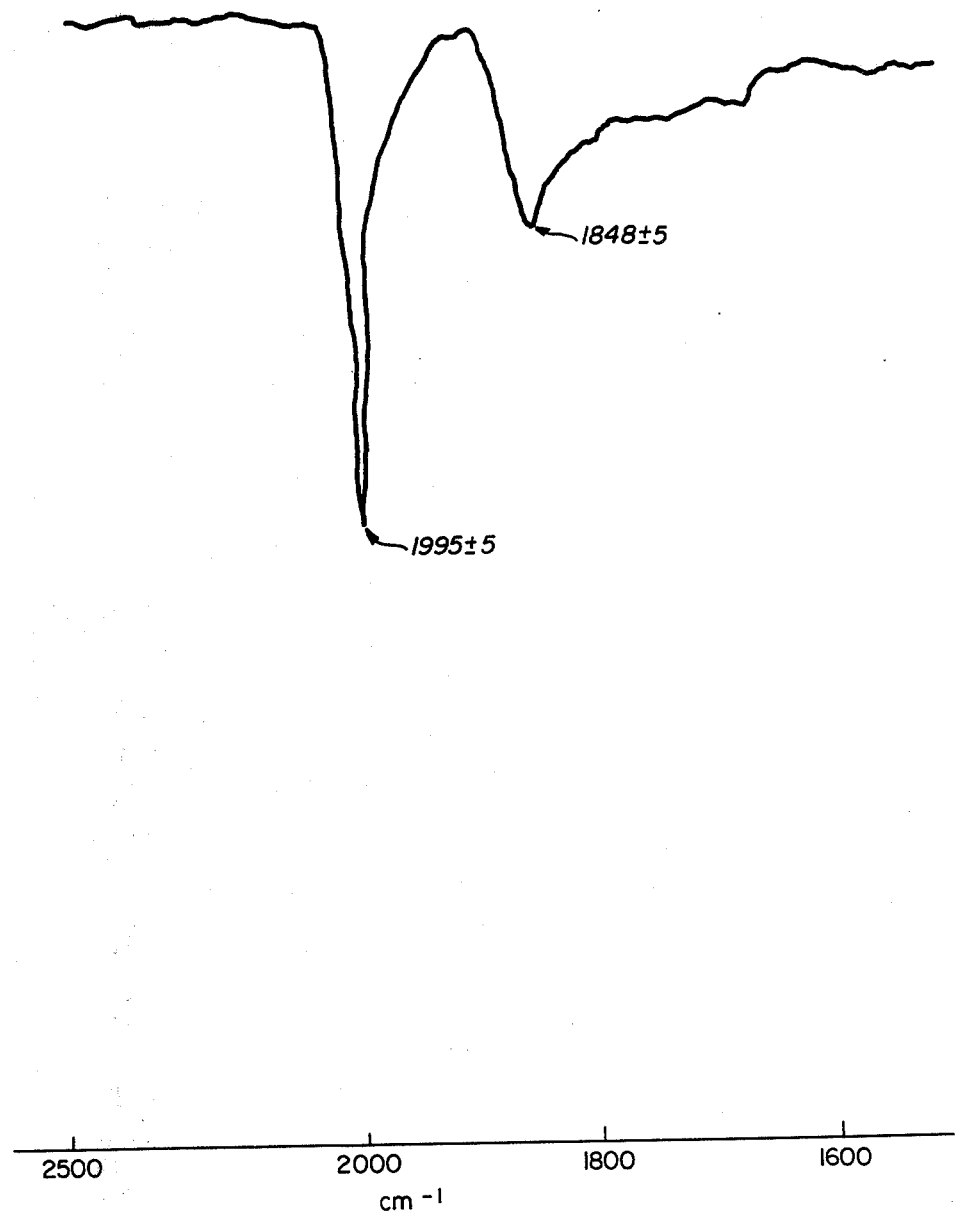

The resulting solids were filtered, washed with dry isopropanol and vacuum dried. The infrared spectral pattern of a sample of this product dissolved in acetone is given FIG. 5 which shows wavelength bans at 1995 cm$^{-1}$ and 1848 cm$^{-1}$, each ±5 cm$^{-1}$.

EXAMPLE 17

Preparation of the Tetraethylammonium Salt of Rh-22 Carbonyl Cluster Anion

Figure 6:
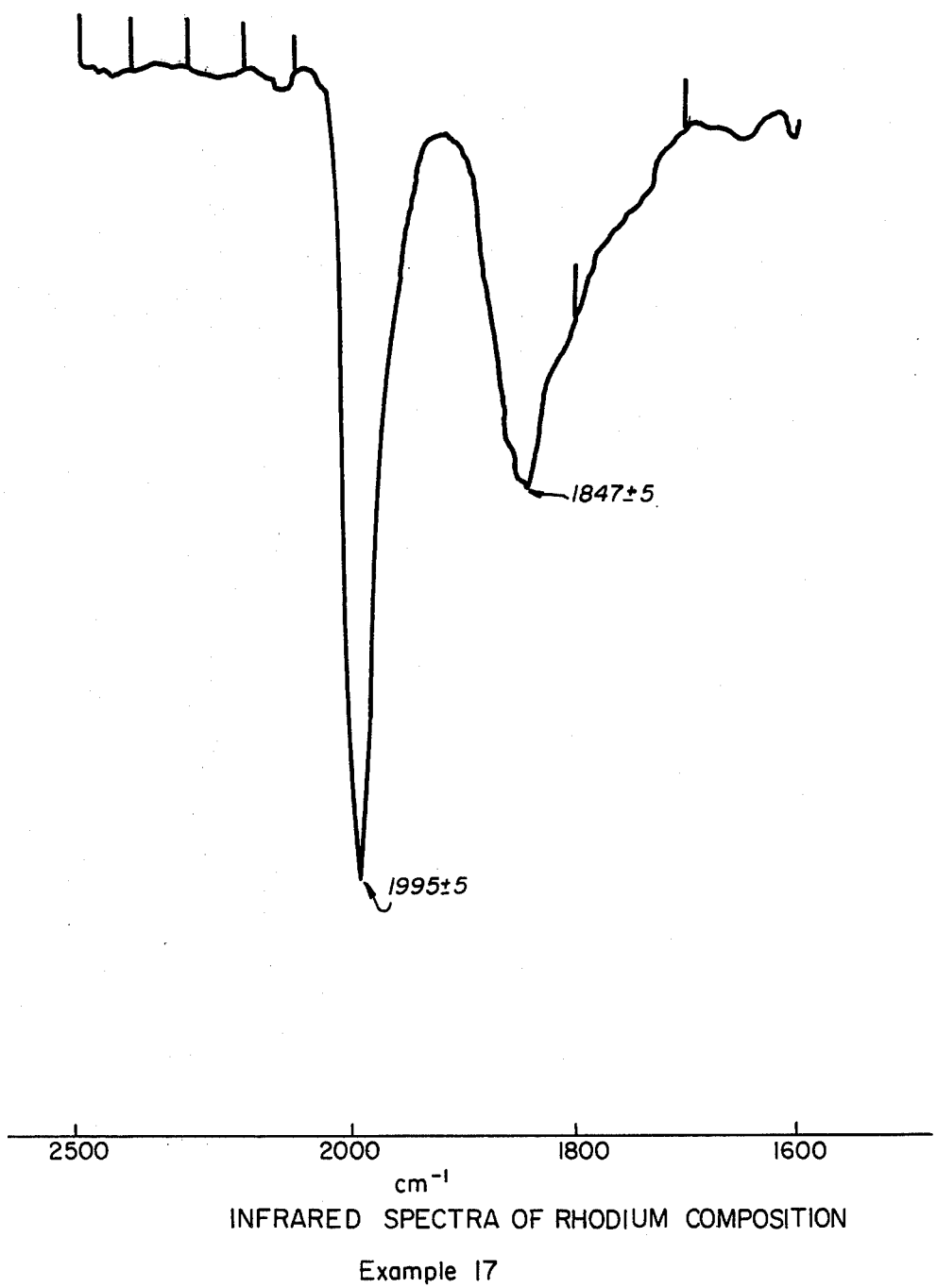

To 154 grams of molten 18-crown-6 ether which had been stirred while sparging with carbon monoxide below the liquid level for about 30 minutes at 70° C., the following were added under carbon monoxide: rhodium dicarbonylacetylacetonate (6.279 grams), cesium benzoate trihydrate (1.4192 grams) and water (13.44 grams). While agitating and sparging with carbon monoxide, the temperature was raised to 155°–160° C. and was left under these conditions for about 17 hours. The solids which formed during this period were separated by filtration and were washed with a large amount of THF until the filtrate was essentially colorless. The washed solids were vacuum dried. Infrared analysis of a sample of the dried solids dissolved in acetone showed bands at 1990 and 1845 cm$^{-1}$ (and a shoulder at 1820 cm$^{-1}$), indicating that the cesium/crown ether salt of the Rh-22 carbonyl cluster described under Example 1 and 2 had formed. About a one-half portion of the dried solids were combined with a solution containing about 1 gram of tetraethylammonium chloride, (C$_2$H$_5$)$_4$NCl, dissolved in 15 ml. of isopropanol to produce the tetraethylammonium salt of the Rh-22 carbonyl cluster anion. The precipitated salt (8-JLV-8B) was recovered by filtration, washed with isopropanol and vacuum dried. The infrared spectral pattern is shown in FIG. 6 and, as indicated, exhibits bands at 1995 and 1847 cm$^{-1}$ with shoulders at 1860, 1855 and 1810 cm$^{-1}$, each ±5 cm$^{-1}$.

What is claimed is:

1. Rhodium carbonyl cluster compounds wherein the cluster comprises twenty-two rhodium atoms.

2. The rhodium cluster compound of claim 1 which is a compound having the following formula:

$$[Rh_{22}(CO)_yH_x][M]_n$$

wherein M is a cation, y usually has a value from about 33 to about 44, X is zero or a positive number having an average value up to about 10, and n corresponds to the charge of the [Rh$_{22}$(CO)$_y$H$_x$] cluster.

3. The rhodium carbonyl cluster compounds of claim 2 wherein M is an inorganic cation, organic cation or an inorganic/organic complex ion.

4. The rhodium carbonyl cluster compound of claim 3 wherein M is any of an ammonium cation, a metal cation, a quaternary ammonium cation, a quaternary phosphonium cation, a bis(triorganophosphine) iminium cation, or a cation-containing hetero-macrocyclic complex wherein the heteromacrocyclic portion is a crown ether or crytand, and the cation which is in complex combination with the heteromacrocyclic compound is a metal cation.

5. The rhodium carbonyl cluster compound of claim 3 wherein M is any of an alkali metal cation, an alkaline earth cation, a transition metal cation, or an aluminum, zinc, chromium or zirconium cation.

6. The rhodium carbonyl cluster compound of claim 5 wherein M is a transition metal cation selected from the group of iron, cobalt and iridium.

7. The rhodium carbonyl cluster compound of claim 2 wherein the charge n on the anionic rhodium carbonyl cluster portion is 0, −1, −2, −3, −4 or −5.

8. The rhodium carbonyl cluster compound of claim 7 wherein the charge n on the anionic rhodium carbonyl cluster portion is −3, −4 or −5.

UNITED STATES PATENT AND TRADEMARK OFFICE
CERTIFICATE OF CORRECTION

PATENT NO. : 4,320,064
DATED : March 16, 1982
INVENTOR(S) : Jose L. Vidal

It is certified that error appears in the above—identified patent and that said Letters Patent is hereby corrected as shown below:

Col. 3, line 29 "61,465" should read --61,456--.

Col. 5, line 14 "$R_6$--P__N--P__$R_9$" should read --$R_6-\underset{R_7}{\overset{R_5}{P}}--N--\underset{R_{10}}{\overset{R_8}{P}}-R_9$--.

Col. 10, line 14 "7],[Rh" should read --7][Rh--.

Col. 12, line 57 "$FM_{TM}$" should read --$FM^{TM}$--.

Col. 14, line 24, insert the words --(77.28 grams), rhodium dicarboxylacetonate (3.1304 grams) and cesium benzoate trihydrate (0.7096 grams) dissolved in 6.72 grams of water. While stirring the solution and sparging carbon monoxide below the liquid level, the temperature was held at 150° - 155°C. for -- before the words "about 17 hours." and delete the words in column 14, line 66 through and including line 70.

Signed and Sealed this

Fourteenth Day of December 1982

[SEAL]

Attest:

GERALD J. MOSSINGHOFF

Attesting Officer

Commissioner of Patents and Trademarks